United States Patent
Park et al.

(10) Patent No.: US 9,470,666 B2
(45) Date of Patent: Oct. 18, 2016

(54) PINHOLE INSPECTION SYSTEM AND APPARATUS FOR MEMBRANE ELECTRODE ASSEMBLY OF FUEL CELL

(71) Applicant: Hyundai Motor Company, Seoul (KR)

(72) Inventors: Ji Yeon Park, Gyeonggi-do (KR); Bo Ki Hong, Seoul (KR); Sang Yeoul Ahn, Seoul (KR)

(73) Assignee: Hyundai Motor Company, Seoul (KR)

( * ) Notice: Subject to any disclaimer, the term of this patent is extended or adjusted under 35 U.S.C. 154(b) by 759 days.

(21) Appl. No.: 13/686,356

(22) Filed: Nov. 27, 2012

(65) Prior Publication Data

US 2014/0030815 A1    Jan. 30, 2014

(30) Foreign Application Priority Data

Jul. 30, 2012 (KR) .................. 10-2012-0083253

(51) Int. Cl.
| | |
|---|---|
| *G01N 21/00* | (2006.01) |
| *G01M 3/04* | (2006.01) |
| *G01N 31/22* | (2006.01) |

(52) U.S. Cl.
CPC ............ *G01N 31/221* (2013.01); *G01N 31/22* (2013.01)

(58) Field of Classification Search
CPC ............ C02F 2201/46115; C02F 2201/4612; C02F 2209/06; C02F 1/46109; C02F 2209/30; C02F 2209/005; C02F 2305/026; C02F 1/46; H01M 2008/1095; H01M 2250/30; H01M 8/0656; H01M 2300/0082; H01M 8/04067; H01M 8/04291; G01N 2035/00326; G01N 31/22; G01N 21/25; G01N 31/221; A01N 25/10; A61L 2/035
See application file for complete search history.

(56) References Cited

U.S. PATENT DOCUMENTS

| | | | |
|---|---|---|---|
| 5,763,765 A | 6/1998 | Lamont et al. | |
| 2009/0131617 A1* | 5/2009 | Thorn et al. | 526/340.3 |

FOREIGN PATENT DOCUMENTS

| | | |
|---|---|---|
| JP | 2004-233097 | 8/2004 |
| JP | 2005-134218 A | 5/2005 |
| JP | 2005123101 A | 5/2005 |
| JP | 2005181013 A | 7/2005 |
| JP | 2008311060 A | 12/2008 |
| KR | 10-1021121 | 10/2009 |

OTHER PUBLICATIONS

Houghton, "Field Confirmation Testing for Suspicious Substances", CRC Press, 2009, Taylor&Francis Group, LLC, p. 347.*

* cited by examiner

*Primary Examiner* — Yelena G Gakh
(74) *Attorney, Agent, or Firm* — Mintz Levin Cohn Ferris Glovsky and Popeo, P.C.; Peter F. Corless

(57) ABSTRACT

Disclosed is a pinhole inspection apparatus, system and method for a membrane electrode assembly of a fuel cell, which can easily detect the position of a pinhole using water and a pH test paper from discoloration caused when the water is in contact with the pH test paper through the pinhole, thus solving the existing problems and allowing the membrane electrode assembly to be reused after the inspection. In particular, a lower fixture is configured to support the membrane electrode assembly and water is uniformly distributed on an upper surface of the membrane electrode assembly. A pH test paper is inserted between the membrane electrode assembly and the lower fixture and discolored upon coming in contact with water that passes through a pinhole in the membrane electrode assembly, thus detecting the presence and position of the pinhole.

11 Claims, 6 Drawing Sheets

PINHOLE INSPECTION SYSTEM AND APPARATUS FOR MEMBRANE ELECTRODE ASSEMBLY OF FUEL CELL

CROSS-REFERENCE TO RELATED APPLICATION

This application claims under 35 U.S.C. §119(a) the benefit of Korean Patent Application No. 10-2012-0083253 filed Jul. 30, 2012, the entire contents of which are incorporated herein by reference.

BACKGROUND (a) Technical Field

The present invention relates to a pinhole inspection system and apparatus for a membrane electrode assembly (MEA) of a fuel cell, which detects the presence and position of a pinhole without damaging or destroying of one or more parts in the MEA.

(b) Background Art

A fuel cell is an energy conversion device that does not convert chemical energy of fuel into heat by combustion, but instead electrochemically converts the chemical energy directly into electrical energy. The fuel cell can then be used for the supply of electric power to small-sized electrical/electronic devices such as portable devices, as well as for the supply of electric power to industrial, domestic, and vehicle applications.

Typically, a polymer electrolyte membrane fuel cell (PEMFC) having high power density is conventional used as a fuel cell source in a vehicle. The polymer electrolyte membrane fuel cell has many advantages such as a low operating temperature of 50 to 100° C., fast startup and power conversion rate, and high energy density.

Structurally, a fuel cell in formed into a fuel cell stack by positioning a membrane electrode assembly (MEA) in the center of each unit cell of the fuel cell stack. The MEA comprises a solid polymer electrolyte membrane, through which hydrogen ions are transported, and catalyst layers including a cathode and an anode, which are coated on both sides of the electrolyte membrane so that hydrogen reacts with oxygen.

Moreover, a gas diffusion layer (GDL) and a gasket are sequentially stacked on the outside of the electrolyte membrane, i.e., where the cathode and the anode are positioned, respectively. A separator (also called a bipolar plate) including flow fields, through which reactant gases (hydrogen as a fuel and oxygen or air as an oxidant) are supplied and coolant passes therethrough, is positioned on the outside of the GDL. Then, a plurality of unit cells are stacked, and an end plate for supporting the unit cells is attached to each of the outermost sides so that the unit cells can be arranged and fastened between the end plates, thus constructing a fuel cell stack.

As one can image, deterioration of the polymer electrolyte membrane, a core component of the fuel cell, has significant effects on the degradation in performance of the PEMFC. In particular, the deterioration of the electrolyte membrane occurs via a mechanism represented by the following Reactions (1) to (3).

Reaction (1):

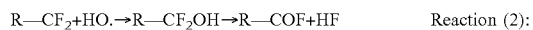
Reaction (2):

Reaction (3):

Referring to the above Reaction s, oxygen diffusing through the membrane from the cathode is converted into hydrogen peroxide in the presence of a platinum (Pt) catalyst and diffuses to the electrolyte membrane. Here, when the membrane is contaminated by metal ions, hydroxyl radicals (HO.) and hydroperoxyl radicals (HOO.) are produced by a reaction between hydrogen peroxide and metal ions. These radicals attack the end groups of the membrane to cause chain scission in the polymer chains of the membrane, thus deteriorating the polymer electrolyte membrane.

When the scission of the polymer chains is repeated by the above chemical deterioration, the elastomeric polymer may become thin, or local pinholes or cracks, etc., may occur. These deterioration effects are associated with the degradation in performance of the fuel cell stack. Accordingly, it is necessary to detect the presence and position of the pinhole in the polymer electrolyte membrane in order to prevent the degradation in performance of the fuel cell stack.

Conventional techniques to detect the presence and position of the pinhole in the polymer electrolyte membrane will now be described.

First, as shown in FIG. 1, Japanese Patent Publication No. 2004-233097 discloses a hydrogen sensor 5 that includes a microcapsule means 1 for covering the powder particles of a hydrogen-occlusion alloy with a metal film, a temperature detection means by a thermocouple 2, an integration means, where the covered powder particles of the hydrogen occlusion alloy of the microcapsule means 1 and the thermocouple 2 of the temperature detection means are accommodated in an end cap of a fuse 3, and an electronic control means by an electronic control unit 4 including a power supply.

However, when the pinhole of the membrane electrolyte assembly is inspected using the hydrogen sensor disclosed in the above Japanese Patent Publication document, only the amount (concentration) of hydrogen gas passing through the pinhole can be detected. It is not possible to measure the position or size of the pinhole.

Secondly, FIG. 2 is a schematic diagram showing a conventional method for detecting a pinhole in a polymer electrolyte membrane using ammonia, in which diluted ammonia ($NH_3$) gas is applied to one side of a polymer electrolyte membrane 11 through a gas flow field 12, and a pH indicator 13 (Filter Paper with Congo Red) is installed on the other side, thus detecting the pinhole in the polymer electrolyte membrane 11 via an Ammonia ($NH_3$) Gas Method as disclosed in Shinji Kinoshita, Fuel Cell Testing Workshop 2007.

However, ammonia gas is very irritating to the eyes, nose, and throat and, the exposure to ammonia gas for a long period of time may cause breathing difficulties, which is very harmful to humans. Accordingly, when the inspection of the pinhole is performed by the above method, it is impossible to perform a total inspection for a long period of time and reuse the polymer electrolyte membrane electrode assembly after the inspection.

Third, as shown in FIG. 3, Korean Patent Application Publication No. 10-2009-0107610, filed by the present applicant, which is hereby incorporated in its entirety by reference, illustrates an apparatus and method for detecting the position of a pinhole in a polymer electrolyte membrane. In particular, an upper block 20 and a lower block 21, in which solutions having different pH values are stored, respectively. An indicator inlet 22 penetrates the top of the upper block 20, and a pair of intermediate plates 23a and 23b are disposed between the upper block 20 and the lower block 21. A lattice-type support net 25 is attached to a support net installation area 24 in the middle of the pair of intermediate plates 23a and 23b, and a polymer electrolyte membrane 25 whose edge is fixed between the pair of intermediate plates 23a and 23b and whose center is placed on the support net, so that the solutions having different pH values can be brought into contact with both sides of the polymer electrolyte membrane 27. Then an indicator 26 is injected into the one side of the polymer electrolyte membrane 25 to cause deterioration, thus easily detecting the position of a pinhole formed in the polymer electrolyte membrane 25 by the deterioration.

During the detection of the presence of the pinhole in the polymer electrolyte membrane 25 using the above method, the polymer electrolyte membrane 25 is exposed to acidic or alkaline pH solutions and thus cannot be reused after the inspection, and the waste solutions are difficult to treat and cause environmental pollution. Therefore, although effective are not ideal.

Lastly, FIG. 4 is a schematic diagram showing a conventional method and apparatus for detecting the presence of a pinhole 31 in a polymer electrolyte membrane using an infrared camera 30 as is disclosed in U.S. Pat. No. 5,763, 765. In this patent, a polymer electrolyte membrane electrode assembly is fixed to a fixture, air is injected into one side thereof, and hydrogen is injected into the other side thereof. If there is a pinhole in the polymer electrolyte membrane electrode assembly, the two gases meet through the pinhole to cause an exothermic reaction in the presence of a platinum (Pt) catalyst. Here, the temperature distribution is measured by an infrared camera 30, and thus the point at which the temperature increases locally is determined as the position of the pinhole 31. The numeral 32 denotes a pinhole detection monitor, and 33 denotes an electrical signal analyzer.

However, when an infrared camera 30 is used, hydrogen gas is injected into a confined space and then pressurized, and thus the membrane may be torn by this process. Moreover, when the exothermic reaction between hydrogen and air occurs suddenly at high temperature during the pressurization, the polymer electrolyte membrane may be burned as well, thus rendering it unusable.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention provides a pinhole inspection system and apparatus for a membrane electrode assembly (MEA) of a fuel cell, which can easily detect the position of a pinhole using water and a pH test paper from discoloration caused when the water is in contact with the pH test paper through the pinhole, thus solving the existing problems and allowing the membrane electrode assembly to be reused after the inspection.

In one aspect, the present invention provides a pinhole inspection system and apparatus for a membrane electrode assembly for a fuel cell, the apparatus includes a lower fixture which is configured to support the membrane electrode assembly, water which is uniformly distributed on an upper surface of the membrane electrode assembly, and a pH test paper which is inserted between the membrane electrode assembly and the lower fixture and discolored upon contact with the water passing through a pinhole, which is present in the membrane electrode assembly, thus detecting the presence and position of the pinhole.

In an exemplary embodiment, the system and apparatus may further include an upper fixture which presses the top of the membrane electrode assembly so that the water can be easily absorbed by the pH test paper through the pinhole. Additionally, a slip sheet which is placed to cover the top of the membrane electrode assembly, may maintain the cleanliness of the membrane electrode assembly allowing the membrane to be reused.

In still another exemplary embodiment, the water may be supplied to an electrode surface of the membrane electrode assembly using a pipette or a flow field. Additionally, the pH test paper may be discolored upon contact with the water at pH 7 so that the discoloration can be compared with a standard color chart.

Other aspects and exemplary embodiments of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
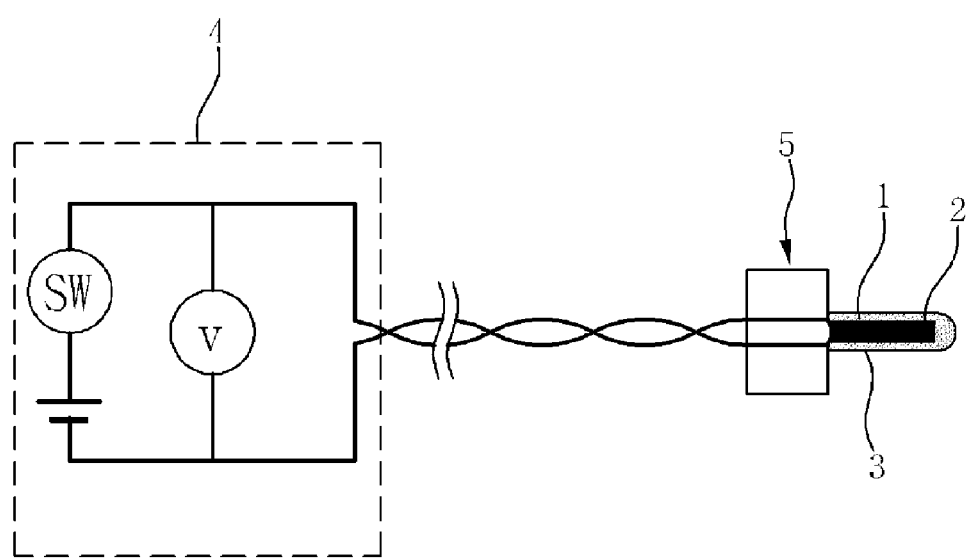
FIG. 1 is a schematic diagram showing a conventional hydrogen sensor.
Figure 2:
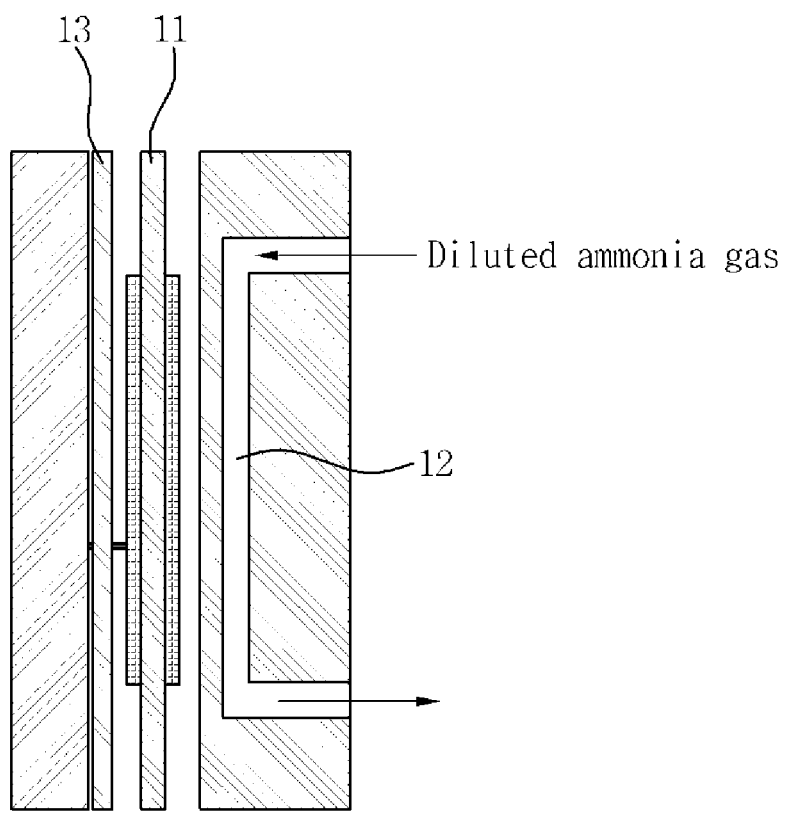
FIG. 2 is a schematic diagram showing a method for detecting a pinhole in a polymer electrolyte membrane using ammonia according to another conventional method.
Figure 3:
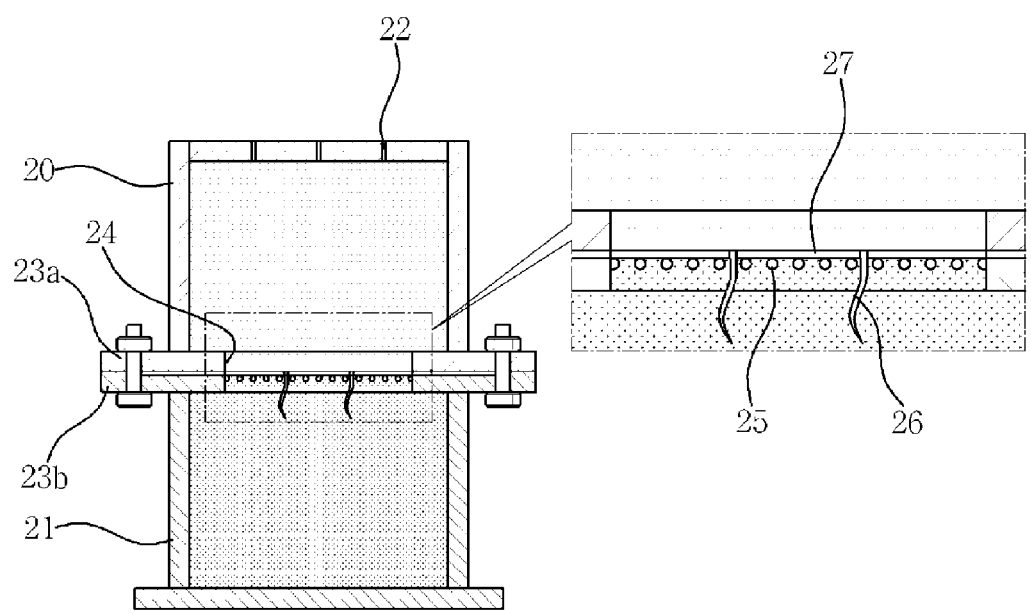
FIG. 3 is a schematic diagram showing an apparatus for detecting the position of a pinhole in a polymer electrolyte membrane according to a yet another conventional apparatus.
Figure 4:
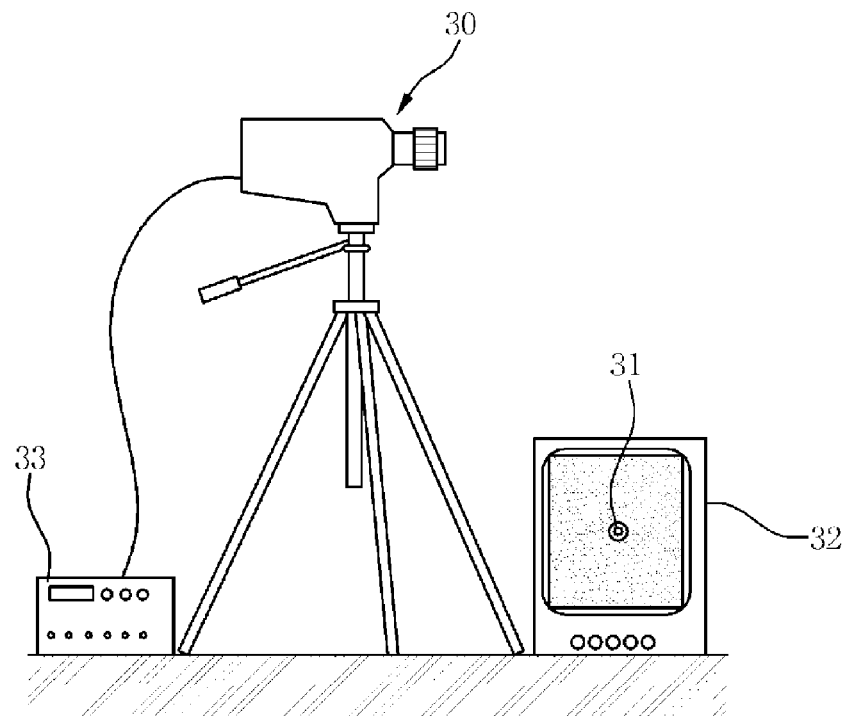
FIG. 4 is a schematic diagram showing a method for detecting the presence of a pinhole in a polymer electrolyte membrane using an infrared camera according to still yet another conventional method.

Reference numerals set forth in the Drawings includes reference to the following elements as further discussed below:

| | |
|---|---|
| 50: upper fixture | 51: handle |
| 52: lower fixture | 53: pH test paper |
| 54: slip sheet | 55: membrane electrode assembly |
| 56: deionized water | 57: pinhole |
| 60: upper fixture | 61: lower fixture |
| 62: pH test paper | 63: gasket |
| 64: membrane electrode assembly | 65: bolt |
| 66: flow field | 66a: inlet |
| 66b: intermediate flow field | 66c: outlet |
| 67: deionized water | 68: pinhole |

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

The above and other features of the invention are discussed infra.

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

Figure 5:
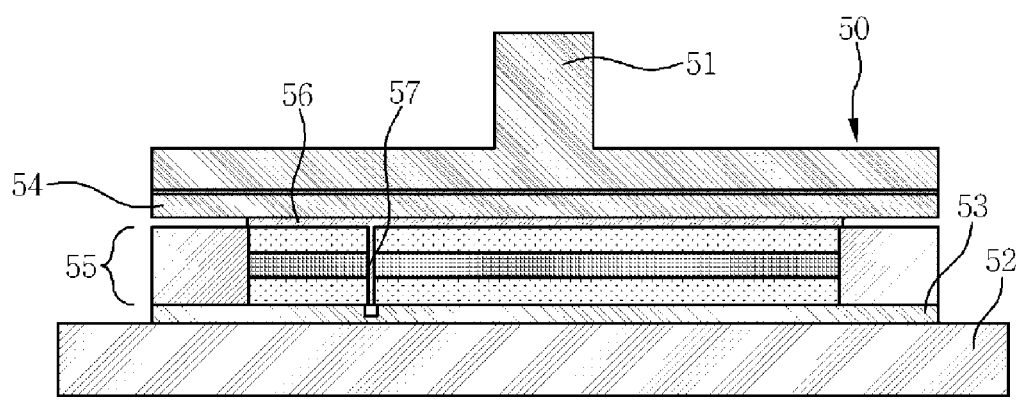
FIG. 5 is a cross-sectional view showing a pinhole inspection apparatus for a membrane electrode assembly for a fuel cell in accordance with an exemplary embodiment of the present invention.

FIG. 5 is a cross-sectional view showing a pinhole inspection apparatus for a membrane electrode assembly for a fuel cell in accordance with an exemplary embodiment of the present invention. The present invention provides a pinhole inspection apparatus, system and method for a membrane electrode assembly 55 of a fuel cell, which can easily detect the position of a pinhole 57, enable a pre-inspection and a post-deterioration analysis, and allow the membrane electrode assembly 55 to be reused after the inspection, without damaging or destroying of one or more portions in the membrane electrode assembly 55. To this end, the pinhole inspection apparatus simply detects the presence, position, and size of a pinhole formed in a polymer electrolyte membrane of the membrane electrode assembly 55 via using deionized water 56 and a pH test paper 53.

First, the pinhole inspection apparatus generally includes a lower fixture 52 configured to support and fix a polymer membrane electrode assembly 55 (hereinafter referred to as a membrane electrode assembly(MEA)), a pH test paper 53 configured to detect the position of a pinhole 57 in the membrane electrode assembly 55, and an upper fixture 50 configured to press the membrane electrode assembly 55 so that the deionized water 56 can be uniformly distributed on the upper surface of the membrane electrode assembly 55. The lower fixture 52 serves to support the membrane electrode assembly 55 and has a flat plate shape so that the membrane electrode assembly 55 can be placed thereon to be stably supported.

The pH test paper 53 is in the form of a tape prepared by dyeing a filter paper such as litmus paper with an acid-base indicator and is used to measure the pH. Preferably, the pH test paper 53 has the same size as the actual membrane electrode assembly 55 in order to be able to detect the position of the pinhole 57.

The membrane electrode assembly 55 is placed on the pH test paper 53 and, when there is a pinhole 57 in the membrane electrode assembly 55, the deionized water 56 passes through the pinhole 57 and comes in contact with am indicator within the pH test paper 53 to cause a discoloration in the test paper 53, from which it is possible to detect the presence and position of the pinhole 57.

The upper fixture 50 has a flat plate shape and presses on the upper surface of the membrane electrode assembly 55 so that the deionized water 56 supplied onto the upper surface of the membrane electrode assembly 55 can be uniformly distributed, thus allowing the deionized water 56 to be rapidly absorbed by the pH test paper 53 through the pinhole 57.

A handle 51 may be formed to project from the top of the upper fixture 50 to be used to hold and carry the upper fixture 50 or transmit the pressing force to the top of the membrane electrode assembly 55 through the upper fixture 50.

A slip sheet 54 may be inserted between the membrane electrode assembly 55 and the upper fixture 50. When the membrane electrode assembly 55 is pressed by the upper fixture 50, the slip sheet 54 prevents the upper fixture 50 from coming in direct contact with the membrane electrode assembly 55 to prevent foreign substances attached on contact surface of the upper fixture 50 from being transferred to the membrane electrode assembly 55, thus maintaining the initial cleanliness of the membrane electrode assembly 55, which allows the membrane electrode assembly 55 to be reused after the inspection of the pinhole 57.

The pinhole inspection method according to the present invention will now be described.

A pH test paper 53 having the same size and shape as the membrane electrode assembly 55 is placed on the lower fixture 52, and the membrane electrode assembly 55 is placed on the pH test paper 53. Then, the deionized water 56 is uniformly sprayed on an electrode surface of the membrane electrode assembly 55 using, e.g., a pipette. The slip sheet 54 is maintained continuously on the membrane electrode assembly 55 on which the deionized water 56 is sprayed, and then the upper fixture 50 is pressed down.

Figure 7:
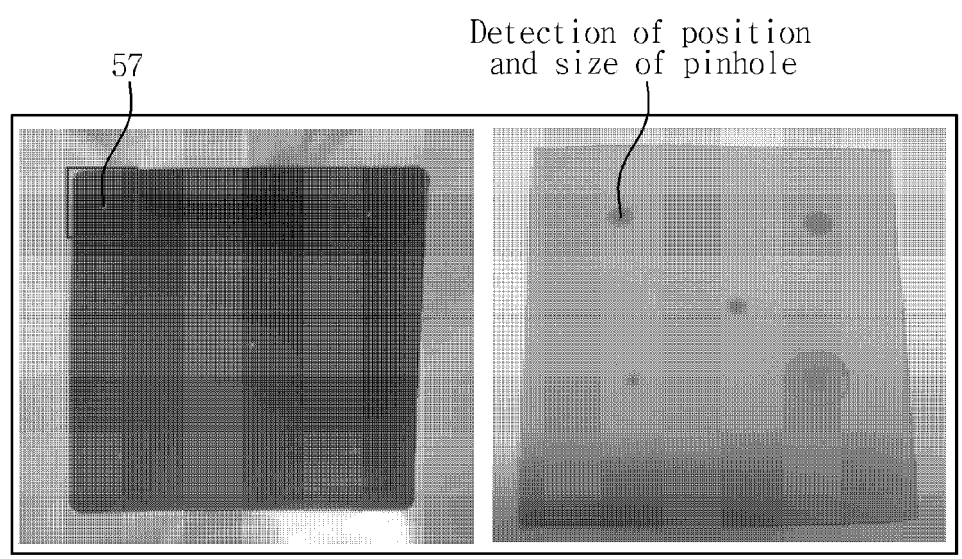
FIG. 7 shows images of a representative example of the detection of the presence and position of a pinhole using the pinhole inspection apparatus in accordance with the exemplary embodiments of the present invention.

Here, when there is a pinhole 57 in the membrane electrode assembly 55, the deionized water 56 passes through the pinhole 57 and is in contact with the pH test paper 53, and thus the pH test paper 53 is discolored to a reaction color at pH 7 (for example, red in FIG. 7). As a result, it is possible to detect the presence and position of the pinhole 57 in the membrane electrode assembly 55 from the associated discoloration.

However, when the upper fixture 50 is pressed for a long time unnecessarily, for example, for more than 1 minute, the deionized water 56 is spread through the membrane electrode assembly 55, which discolors the entire pH test paper 53, thus making it impossible to detect the position of the pinhole 57. Accordingly, it is preferable that the upper fixture 50 be pressed for less than 1 minute to ensure the accuracy of the test.

Therefore, the pinhole inspection apparatus according to the present invention can detect the presence of the pinhole 57 using water such as the deionized water 56. Water is also a product of the electrochemical reaction in the fuel cell, and thus the water as the product of the fuel cell may be used.

Advantageously, water comes in contact with the pH test paper 53 through the pinhole 57 making it possible to rapidly and easily detect the presence and position of the pinhole 57 due to the discoloration of the pH test paper 53 without damaging or destroying one or more portions of the membrane electrode assembly.

Furthermore, the pre-inspection and the post-deterioration analysis are possible, the structure and use of the apparatus is simple, and thus it is possible to ensure excellent workability and working efficiency. Third, since the slip sheet 54 is placed on the membrane electrode assembly 55 and then the upper fixture 50 is pressed down, it is possible to maintain the initial cleanliness of the membrane electrode assembly 55, which allows the membrane electrode assembly 55 to be used for the manufacturing of the fuel cell stack without any additional processing such as the preparation of a separate sample.

Fourth, since the presence and position of the pinhole 57 can be detected by the use of water, the use of ammonia gas, that is very irritating to the eyes, nose, and throat, does not have to be used, thus it is possible to prevent any harm to workers during the inspection process. Moreover, since hydrogen is also not used, it is possible to prevent the electrolyte membrane from becoming burned by consecutive reactions in the presence of a catalyst.

Fifth, acidic or alkaline pH solutions are not used during the inspection of the pinhole, and thus it is possible to reuse the membrane electrode assembly after the inspection and eliminates waste water treatment solutions and environmental pollution.

Figure 6:
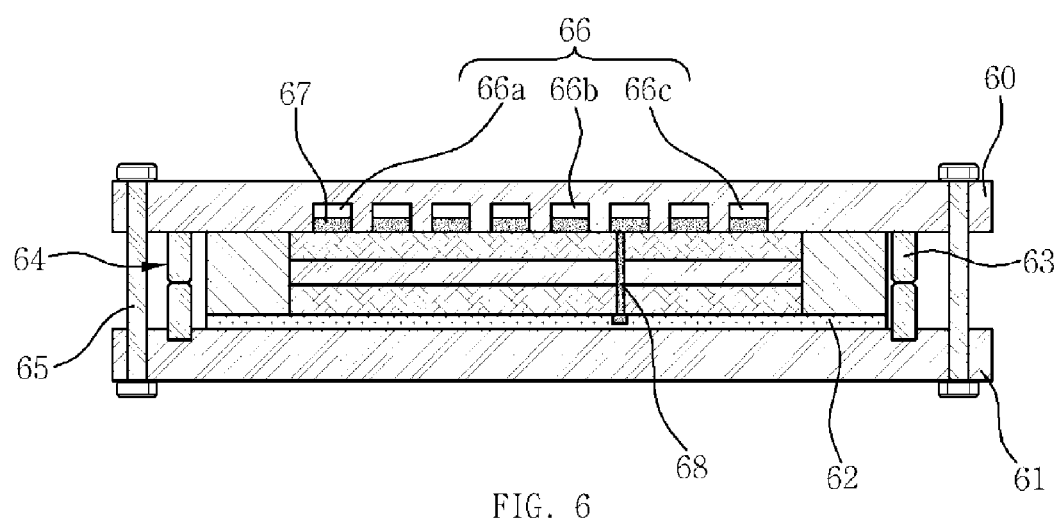
FIG. 6 is a cross-sectional view showing a pinhole inspection apparatus for a membrane electrode assembly for a fuel cell in accordance with another exemplary embodiment of the present invention.

FIG. 6 is a cross-sectional view showing a pinhole inspection apparatus for a membrane electrode assembly for a fuel cell in accordance with another exemplary embodiment of the present invention, and FIG. 7 shows images of a representative example of the detection of the presence and position of a pinhole using the pinhole inspection apparatus in accordance with the exemplary embodiments of the present invention.

In another exemplary embodiment of the present invention, a pinhole inspection apparatus having the same structure as the fixture used in the actual evaluation of the fuel cell is provided.

The pinhole inspection apparatus in accordance with another exemplary embodiment of the present invention comprises an upper fixture 60 having a flow field 66 through which deionized water 67 can flow and a lower fixture 61 which can support a membrane electrode assembly 64 and a pH test paper 62. When a gasket 63 is replaced based on the thickness of the membrane, it is possible to detect a pinhole 68 in membranes of various thicknesses.

Here, the flow field 66 includes an inlet 66a, an intermediate flow field 66b, and an outlet 66c, which are formed from one end of the upper fixture to the other end of the upper fixture so that the deionized water 67 can be uniformly distributed over the entire surface of the membrane electrode assembly 64.

An inspection method according to this embodiment of the present invention, is therefore similar to the previously described method.

In particular, a pH test paper 62 having the same size and shape as a sample to be inspected is placed on the lower fixture 61, the membrane electrode assembly 64 is placed thereon, and then the upper fixture 60 and the lower fixture 61 are fastened via a bolt 65. Then, the deionized water 67 is injected through the flow filed 66 of the upper fixture 60, and when there is a pinhole 68 in the membrane electrode assembly 64, the deionized water 67 is in contact with the pH test paper 62, and thus the pH test paper 62 is discolored to a reaction color at pH 7. The discoloration represents the presence of the pinhole 68 in the membrane electrode assembly 64, and thus it is possible to detect the presence and position of the pinhole 68.

As described above, the pinhole inspection apparatus according to the present invention has the following advantages.

First, as the water comes in contact with the pH test paper through the pinhole, it is possible to rapidly and easily detect the presence and position of the pinhole from the discoloration of the pH test paper without damaging or destroying of parts. Second, the pre-inspection and the post-deterioration analysis are possible, the structure and use of the apparatus is simple, and thus it is possible to ensure excellent workability and working efficiency.

Third, since the slip sheet is placed on the membrane electrode assembly and then the upper fixture is pressed down, it is possible to maintain the initial cleanliness of the membrane electrode assembly, which allows the membrane electrode assembly to be used for the manufacturing of the fuel cell stack without any additional process such as the preparation of a separate sample.

Fourth, since the presence and position of the pinhole is detected by the use of water rather than ammonia gas (that is very irritating to the eyes, nose, and throat), it is possible to prevent harm to the workers during the inspection. Moreover, since the hydrogen is not used, it is possible to solve the problem that the electrolyte membrane is burned by the consecutive reaction in the presence of a catalyst.

Fifth, since acidic or alkaline pH solutions are not used during the inspection of the pinhole, it is possible to reuse the membrane electrode assembly after the inspection and thus eliminates waste water treatment solutions and environmental pollution.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. A pinhole inspection apparatus for a membrane electrode assembly of a fuel cell, the apparatus comprising:
   a lower fixture configured to support the membrane electrode assembly;
   deionized water uniformly distributed on an upper surface of the membrane electrode assembly;
   a pH test paper inserted between the membrane electrode assembly and the lower fixture,
   an upper fixture which presses against a top surface of the membrane electrode assembly; and
   a slip sheet which is placed over the top surface of the membrane electrode assembly to prevent debris from being transferred to the membrane electrode assembly,
   wherein when there is a pin hole in the membrane electrode assembly, the pH test paper is discolored upon coming in contact with the deionized water at a pH 7 that passes through the pinhole to detect the presence and position of the pinhole in the membrane electrode assembly, wherein the deionized water is distributed on an electrode surface of the membrane electrode assembly by being supplied to an electrode surface of the membrane electrode assembly using a pipette.

2. The apparatus of claim 1, wherein the upper fixture includes a handle formed on the top thereof.

3. A method for detecting a pin hole in a membrane electrode assembly of fuel cell, the method comprising: providing an pinhole inspection apparatus of claim 1, placing a pH test paper on the lower fixture, and placing the membrane electrode assembly on the pH test paper; uniformly spraying the deionized water on an electrode surface of the membrane electrode assembly; and pressing down on a slip sheet placed over the membrane electrode assembly by an upper fixture; wherein when there is a pinhole in the membrane electrode assembly, the deionized water passes through the pinhole and comes in contact with the pH test paper, and the pH test paper is then discolored as a result of coming in contact with the deionized water.

4. The method of claim 3, wherein the upper fixture is pressed for less than 1 minute.

5. The method of claim 3, wherein the slip sheet placed over the top of the membrane electrode assembly is the same size and shape as the membrane electrode assembly.

6. A pinhole inspection apparatus for a membrane electrode assembly of a fuel cell, the apparatus comprising:
- a lower fixture configured to support the membrane electrode assembly;
- deionized water uniformly distributed on an upper surface of the membrane electrode assembly;
- a pH test paper inserted between the membrane electrode assembly and the lower fixture, an upper fixture which presses against a top surface of the membrane electrode assembly; and
- a slip sheet which is placed over the top surface of the membrane electrode assembly to prevent debris from being transferred to the membrane electrode assembly, wherein when there is a pin hole in the membrane electrode assembly, the pH test paper is discolored upon coming in contact with the deionized water at a pH 7 that passes through the pinhole to detect the presence and position of the pinhole in the membrane electrode assembly, wherein a flow field includes an inlet, an intermediate flow field, and an outlet, which are formed from one end of the upper fixture to the other end of the upper fixture so that the deionized water can be uniformly distributed over the entire surface of the membrane electrode assembly.

7. The apparatus of claim 6, wherein the upper fixture includes a handle formed on the top thereof.

8. A method for detecting a pin hole in a membrane electrode assembly of fuel cell, the method comprising: providing an pinhole inspection apparatus of claim 6, placing a pH test paper on the lower fixture, and placing the membrane electrode assembly on the pH test paper; uniformly spraying deionized water on an electrode surface of the membrane electrode assembly; and pressing down on a slip sheet placed over the membrane electrode assembly by an upper fixture; wherein when there is a pinhole in the membrane electrode assembly, the deionized water passes through the pinhole and comes in contact with the pH test paper, and the pH test paper is then discolored as a result of coming in contact with the deionized water.

9. The method of claim 8, wherein the upper fixture is pressed for less than 1 minute.

10. The method of claim 8, wherein the slip sheet placed over the top of the membrane electrode assembly is the same size and shape as the membrane electrode assembly.

11. The method of claim 8, wherein the water is supplied to an electrode surface of the membrane electrode assembly using the flow field.

* * * * *